US008922549B2

(12) United States Patent
Dorn et al.

(10) Patent No.: US 8,922,549 B2
(45) Date of Patent: Dec. 30, 2014

(54) METHOD AND APPARATUS FOR THE PROGRESSIVE LOADING OF MEDICAL, MULTIDIMENSIONAL IMAGES INTO A MEDICAL APPLICATION

(75) Inventors: Karlheinz Dorn, Kalchreuth (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 341 days.

(21) Appl. No.: 13/552,827

(22) Filed: Jul. 19, 2012

(65) Prior Publication Data

US 2013/0028492 A1 Jan. 31, 2013

(30) Foreign Application Priority Data

Jul. 27, 2011 (DE) .......................... 10 2011 079 916

(51) Int. Cl.
*G06T 15/00* (2011.01)
*G06T 9/00* (2006.01)
*A61B 19/00* (2006.01)
*G06T 15/08* (2011.01)
*G06F 13/00* (2006.01)
*A61B 6/03* (2006.01)
*G06T 1/60* (2006.01)

(52) U.S. Cl.
CPC ... *A61B 6/03* (2013.01); *G06T 9/00* (2013.01); *A61B 19/00* (2013.01); *G06T 15/08* (2013.01); *G06F 13/00* (2013.01); *G06T 2210/41* (2013.01); *G06T 1/60* (2013.01)
USPC .......... 345/419; 382/128; 382/305; 345/420; 345/424

(58) Field of Classification Search
None
See application file for complete search history.

(56) References Cited

U.S. PATENT DOCUMENTS 6,184,889 B1 * 2/2001 D'Amora ...................... 345/419
6,522,336 B1 * 2/2003 Yuasa ............................ 345/582
7,843,452 B2 11/2010 Li
(Continued)

FOREIGN PATENT DOCUMENTS

DE 112004002545 T5 11/2006
WO WO2013/190026 * 12/2013

OTHER PUBLICATIONS

German Priority Document for German Application No. DE 10 2011 079 916.8 filed Jul. 27, 2011 (Not Yet Published).

(Continued)

*Primary Examiner* — Vu Le
*Assistant Examiner* — Samah Beg
(74) *Attorney, Agent, or Firm* — Harness, Dickey & Pierce, P.L.C.

(57) ABSTRACT

A method includes a) loading a first number n of image sets with an image size $k^y$, the $k^y$ images of which are distributed in a regular manner over a volume, which is to be loaded in its entirety as a result; b) loading a number $n^x$ of image sets starting with a factor x=1, with the images loaded in total being distributed in a regular manner over the volume; c) determining a camera distance and voxel size based on the number of images loaded, a camera distance and voxel size being suitable as parameters for a volume rendering; and d) repeating the two preceding steps b) and c) while increasing the number of image sets with a factor x=x+1, until all the images of the volume have been loaded in their entirety and/or until the step sequence ends.

15 Claims, 12 Drawing Sheets

(56) References Cited

U.S. PATENT DOCUMENTS

| | | | |
|---|---|---|---|
| 7,965,290 B1* | 6/2011 | Kouznetsov et al. | 345/419 |
| 2005/0138569 A1 | 6/2005 | Baxter | |
| 2005/0264578 A1* | 12/2005 | Engel et al. | 345/582 |
| 2006/0007244 A1* | 1/2006 | Matsumoto | 345/619 |
| 2006/0114254 A1* | 6/2006 | Day et al. | 345/424 |
| 2007/0186182 A1* | 8/2007 | Schiller | 715/781 |
| 2007/0229501 A1* | 10/2007 | Kouznetsov et al. | 345/424 |
| 2008/0069458 A1* | 3/2008 | Vega-Higuera et al. | 382/232 |
| 2009/0033657 A1* | 2/2009 | Engel et al. | 345/420 |
| 2009/0225076 A1* | 9/2009 | Vlietinck | 345/419 |

OTHER PUBLICATIONS

German Search Report for German Application No. 10 2011 079 916.8 dated Apr. 23, 2012.

* cited by examiner

FIG 3
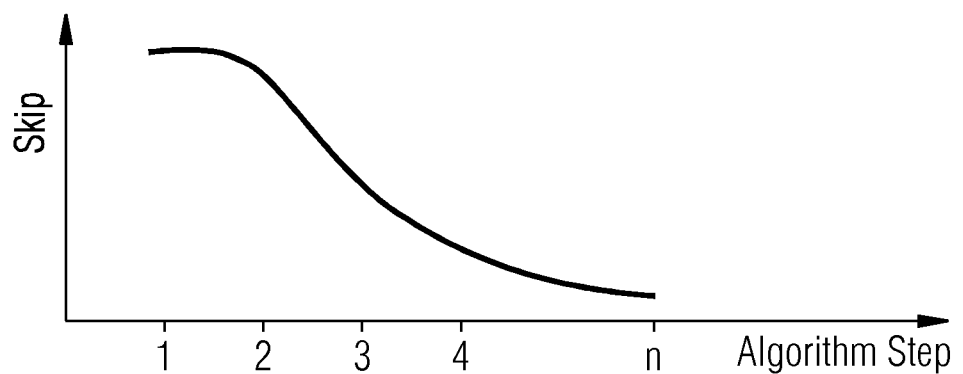
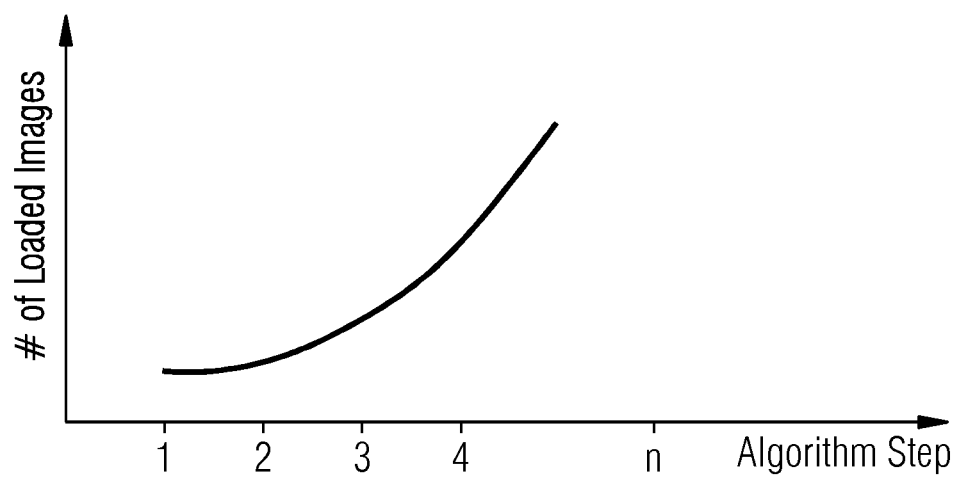

*# Images in Volume: 600*
*Step 1: 1st img to be loaded 8, Skip 8*
*We load images 8, 16, 24, 32, 40, 48, 54, 64, 72, 80, 96, 104, 112, ...*

*# Images in Volume: 600*
*Step 2: 1st img to be loaded 4, Skip 4, if not yet loaded*
*We load images 4, 12, 20, 28, 36, 44, 52, 60, 68, 76, 84, 92, 100, 108, ...*

\# Images in Volume: 600
Step 3: 1st img to be loaded 2, Skip 4, if not yet loaded
We load images 2, 6, 10, 14, 18, 22, 26, 30, 34, 38, 42, 46, 50, 54, ...

\# Images in Volume: 600
Step 4: 1st img to be loaded 1, Skip 2
We load images 1, 3, 5, 7, 9, 11, 13, 15, 17, 19, 21, 23, 25, 27, 29, ...

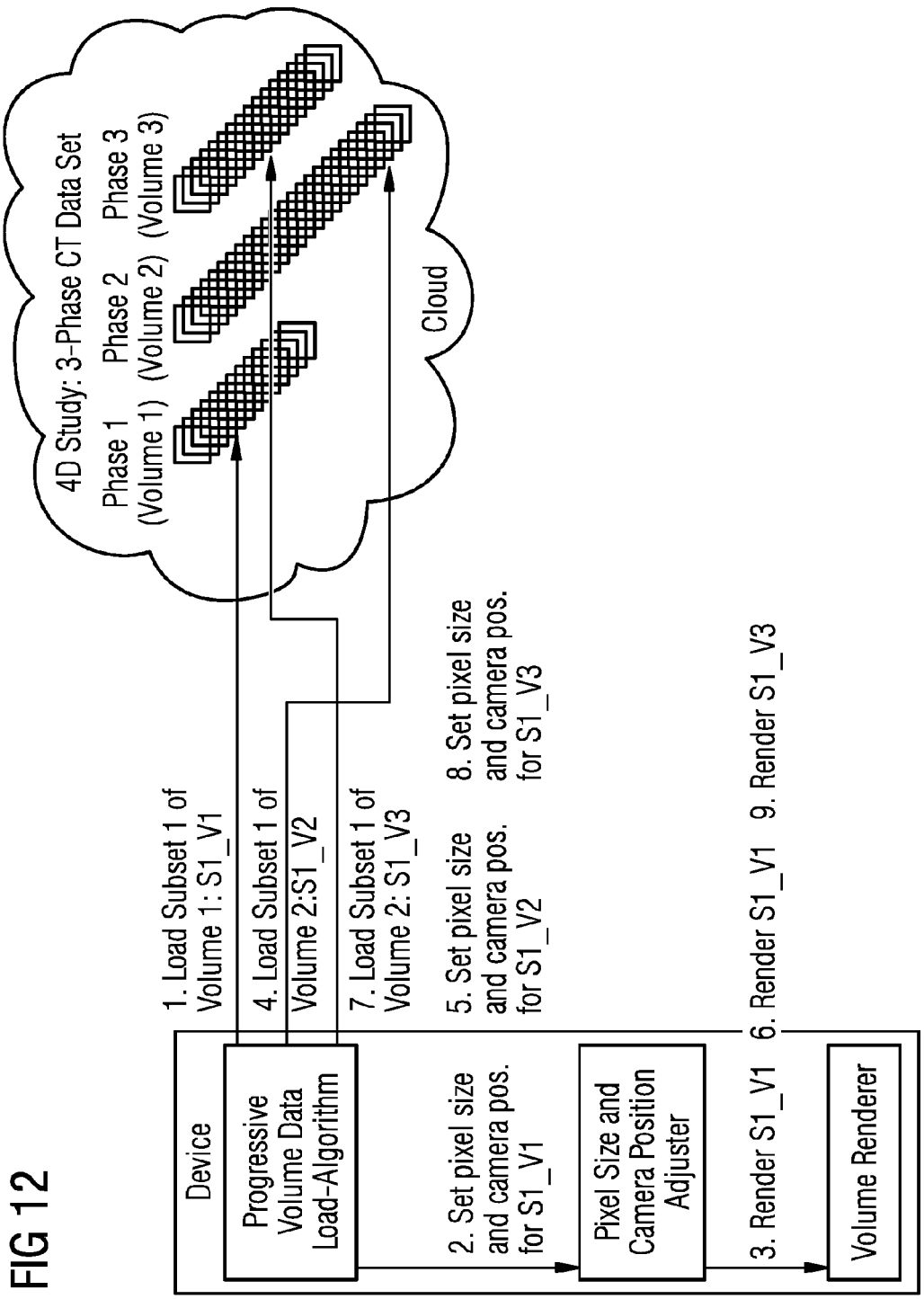

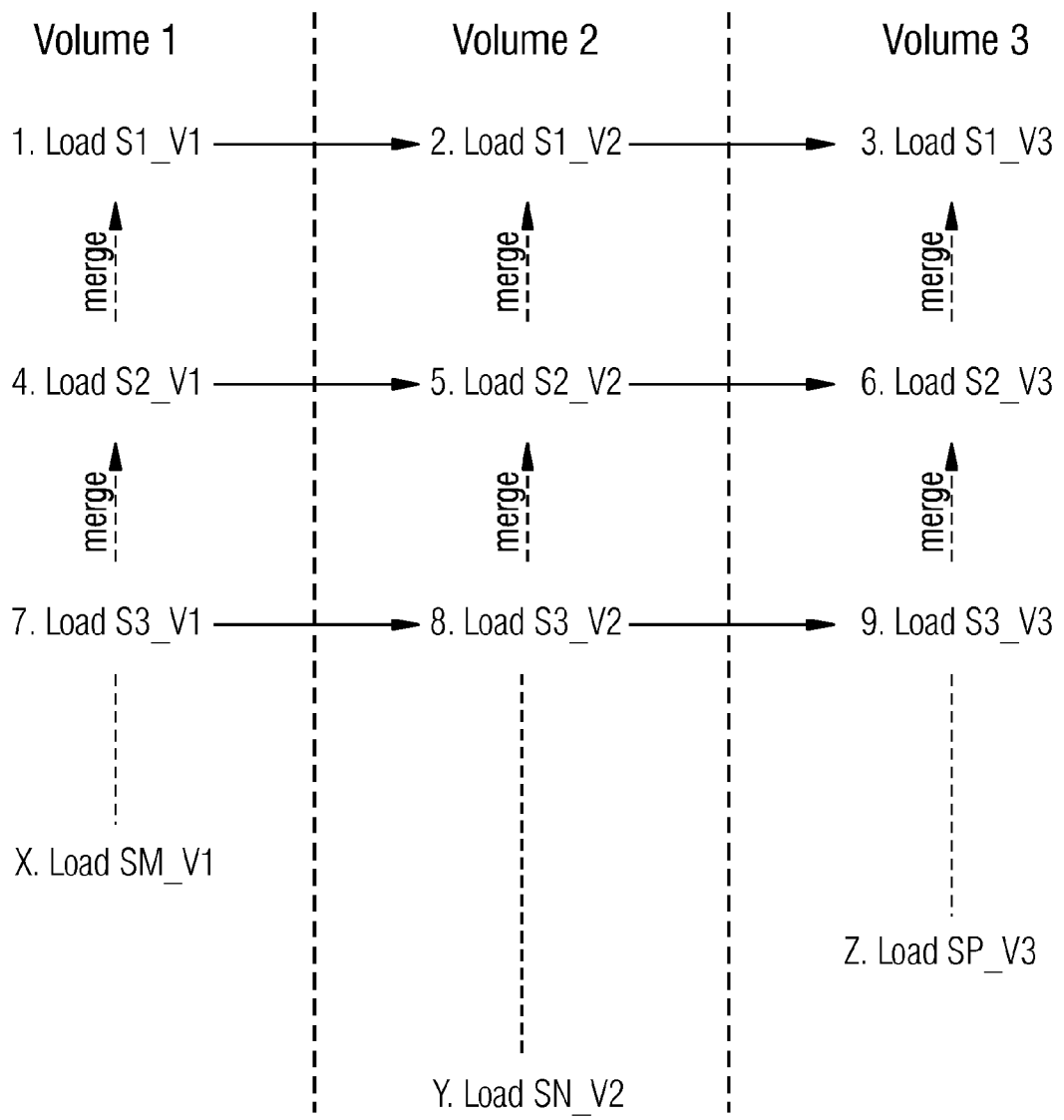

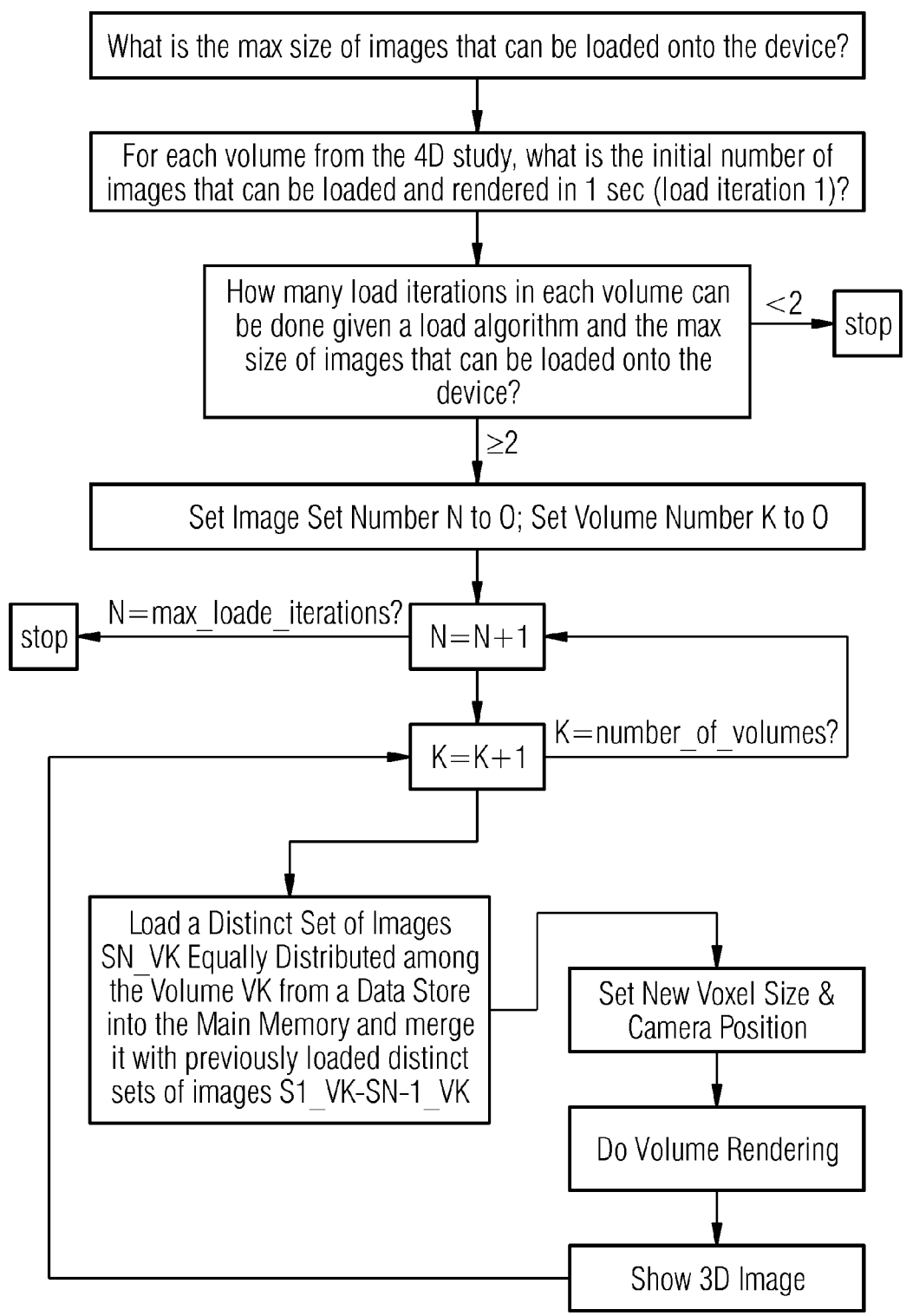

METHOD AND APPARATUS FOR THE PROGRESSIVE LOADING OF MEDICAL, MULTIDIMENSIONAL IMAGES INTO A MEDICAL APPLICATION

PRIORITY STATEMENT

The present application hereby claims priority under 35 U.S.C. §119 to German patent application number DE 10 2011 079 916.8 filed Jul. 27, 2011, the entire contents of which are hereby incorporated herein by reference.

FIELD

At least one embodiment of the invention generally relates to a method and/or apparatus for the progressive loading of medical, multidimensional images into a medical application.

BACKGROUND

A so-called 3D user experience in medical applications essentially includes two components: a) time taken to load the images of a volume from a database or data store into the main memory of the application and b) time taken to produce a 3D image using a so-called volume rendering method.

It is possible with regard to the above point b) to use different algorithms, the algorithms assuming that all the images of a volume are already loaded into the main memory. This is an essential variable, which impacts significantly on the 3D user experience and has not yet been optimized.

Also the data volumes to be loaded into the main memory in the medical field are increasing all the time, as medical modalities increasingly produce larger studies and individual examinations using the modalities often generate not just one but a number of studies, as for example with multirow CT.

Against a background of workflows with very short cycles in medical facilities, it is favorable for the acceptance of medical software that the medical personnel do not have to tolerate waiting times. The software should be able to present multidimensional volumes, in particular 3D or 4D volumes, of any size to the user in such a manner that no waiting times are perceived either when loading the images into the main memory or during volume rendering.

There are methods for improving 3D user experience which perform optimization of volume rendering for images of the volume already loaded into the main memory. This means that the user cannot see a 3D image until all the images of the volume have been loaded into the main memory. Once all the images have been loaded into the main memory, different methods are available for shortening the time required for volume rendering. 3D volume rendering cannot take place until all the images of a medical series have been loaded into the main memory. The bigger the series, the longer the waiting times that have to be tolerated.

One possible method, known as texture-based volume rendering, is based on the volume being divided into distinct three-dimensional so-called bricks and the bricks being rendered one after the other. The quality of the rendered images before all the bricks are loaded in medical imaging in particular can allow diagnosis errors to occur, because one brick represents only one predetermined three-dimensional region of the entire volume. A number of loaded bricks therefore reveal a larger region of the volume, while other regions of the volume remain invisible to the viewer.

One improvement to texture-based volume rendering is the known method of progressive refinement for texture-based volume rendering, as disclosed in U.S. Pat. No. 7,843,452 B2. It is likewise assumed here that all the images of the volume have been loaded into the main memory. Texture-based volume rendering is then used in a modified form, so that the bricks are first loaded with a low resolution and then better and better resolutions of the bricks are continuously loaded until the highest resolution of each brick has been loaded.

The time taken for volume rendering for images already loaded into the main memory is thus optimized. As medical studies become ever larger, the time taken to load the images into the main memory should also be optimized and the volume rendering should be matched to this, in order to achieve a favorable user experience.

SUMMARY

At least one embodiment of the present invention improves the above-mentioned time taken to load the images.

A method and apparatus, as well as a computer program product are disclosed. Advantageous embodiments of the invention are the subject matter of the dependent claims or will emerge from the description which follows and the example embodiments.

According to an embodiment of the invention, a method is provided for the progressive loading of images of a multidimensional volume from a data store or database into the main memory of a client and subsequent, progressive 3D or 4D volume rendering.

An embodiment of the inventive method for the progressive loading of medical, multidimensional images into a medical application comprises:

a) loading a first number n of image sets with an image set size $k^y$, the $k^y$ images of which are distributed in a regular manner over a volume, which is to be loaded in its entirety as a result, b) loading a number $n^x$ of image sets starting with a factor $x=1$, with the images loaded in total in the preceding and current steps being distributed in a regular manner over the volume, c) determining the camera distance and voxel size based on the number of images loaded in the preceding and current steps, with the camera distance and voxel size being suitable as parameters for a volume rendering, and d) repeating the two preceding steps b) and c) while increasing the number of image sets with a factor $x=x+1$, until all the images of the volume have been loaded in their entirety and/or until the step sequence ends.

A further aspect of an embodiment of the invention is directed to an apparatus, preferably a server, for the progressive loading of medical images, having segments or modules for performing at least one embodiment of the abovementioned loading process, which can be configured as a computer program product in hardware and/or software form respectively.

The apparatus and computer program product can be developed according to at least one embodiment of the inventive method.

BRIEF DESCRIPTION OF THE DRAWINGS

Further advantages, details and developments of the invention will emerge from the description which follows of exemplary embodiments in conjunction with the drawings, in which:

FIG. 3 shows a diagram of the curve for certain step widths and a diagram of the curve for a certain number of loaded images, FIG. 12 shows the loading process already illustrated in FIG. 10 in particular with 4D images, FIG. 13 shows the method steps from FIG. 12 shown as 1., 2., 3., etc. in time sequence and FIG. 14 shows an extension of the sequence illustrated in FIG. 1 in conjunction with 4D images.

Figure 1:
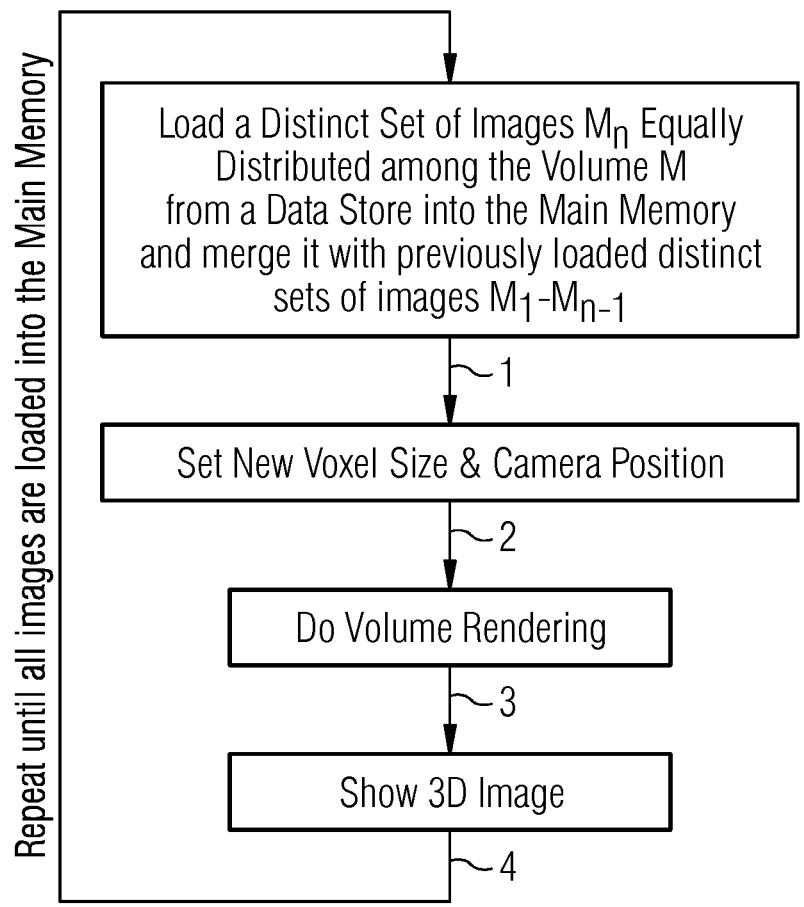
FIG. 1 shows a schematic diagram of an embodiment of an inventive sequence.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the inventive method for the progressive loading of medical, multidimensional images into a medical application comprises:

a) loading a first number n of image sets with an image set size $k^y$, the $k^y$ images of which are distributed in a regular manner over a volume, which is to be loaded in its entirety as a result, b) loading a number $n^x$ of image sets starting with a factor x=1, with the images loaded in total in the preceding and current steps being distributed in a regular manner over the volume, c) determining the camera distance and voxel size based on the number of images loaded in the preceding and current steps, with the camera distance and voxel size being suitable as parameters for a volume rendering, and d) repeating the two preceding steps b) and c) while increasing the number of image sets with a factor x=x+1, until all the images of the volume have been loaded in their entirety and/or until the step sequence ends.

Repetition of the abovementioned steps b) and c) while increasing the image set size with a factor y=y+1 is possible until all the images of the volume have been loaded in their entirety and/or until the step sequence ends. This repetition can also take place before the abovementioned step c).

If y=0, the image set only comprises one image, i.e. as a result there are $n^x$ images, which is favorable for a 3D application of the abovementioned method.

If y=1, the image set comprises k images, which is favorable for a 4D application of an embodiment of the abovementioned method.

The choice of the factors n=2 and k=2 has proved to be advantageous for time-optimized loading of the images and image sets.

The factor $k^y$ can be determined so that the rendering of the volume can be performed within a time interval of 1 second.

A further aspect of an embodiment of the invention is directed to an apparatus, preferably a server, for the progressive loading of medical images, having segments or modules for performing at least one embodiment of the abovementioned loading process, which can be configured as a computer program product in hardware and/or software form respectively.

The apparatus and computer program product can be developed according to at least one embodiment of the inventive method.

The loaded images and image sets can be displayed on a display apparatus.

At least one embodiment of the invention has at least one of the following advantages:

a) Regardless of the size of the 3D volume to be displayed, the user does not perceive any waiting times when working with 3D applications, as both the image loading times and the volume rendering are optimized.

b) If the user terminates a volume rendering process, before all the images of the volume are loaded into the main memory, the remainder of the images are not loaded into the main memory. Since 50% of the images are always loaded in the last step of the loading algorithm, 50% of the loading time is saved, if the user terminates the loading process before the last loading step. At the end of the loading algorithm exponentially ($2^n$) more images are always loaded in each step, so that the time gained on termination of the loading process increases toward the end.

c) The image loading algorithm is independent of the volume rendering algorithm. In other words if the images are loaded in a certain step of the loading algorithm, any volume rendering method can be used to produce the 3D image.

If the device, on which volume rendering is running, has a GPU, said GPU can be used. Otherwise a CPU-based rendering can be deployed.

The method can thus be used both in a so-called public cloud data center, which generally does not have GPUs, as well as on one or more conventional workstations with GPUs.

d) The method allows 3D processing to be performed on client devices, as not all the images of a volume are transferred from the data store to the client before volume rendering takes place. This approach is very economical, as costs would be incurred for commissioning a compute service (processing service) in a data center. A further advantage of 3D processing at the client is the scalability of the system. If 3D processing is performed at the server, server capacities have to be extended as the number of clients increases. This has both a technical and an economic impact. In technical terms every server farm has natural capacity limits. In economic terms the server farm becomes more expensive, the more servers are used. When the invention is applied, the scalability problem does not arise either in technical or economic terms, as no servers are used in the data center, processing being performed at the respective client.

e) The method functions regardless of the storage medium and storage site of the data. The data can be filed in any data store. The data can also be stored either in a local data system or in a local VHD (virtual hard drive) or in a VHD in the cloud.

f) The method functions regardless of the data format. For example the images can be filed in JPEG or in Raw or in DeepZoom format. The images only have to be accessible by way of a URL or by way of a data system application or API.

g) The method can be used in online or real-time scenarios, which require the images to be presented to the user in 3D immediately after being recorded by the modality.

h) The method can be used in 4D scenarios which require regeneration of the volume over time.

i) 3D volume rendering generally takes place without waiting times, regardless of the size of the volume to be loaded.

Figure 2:
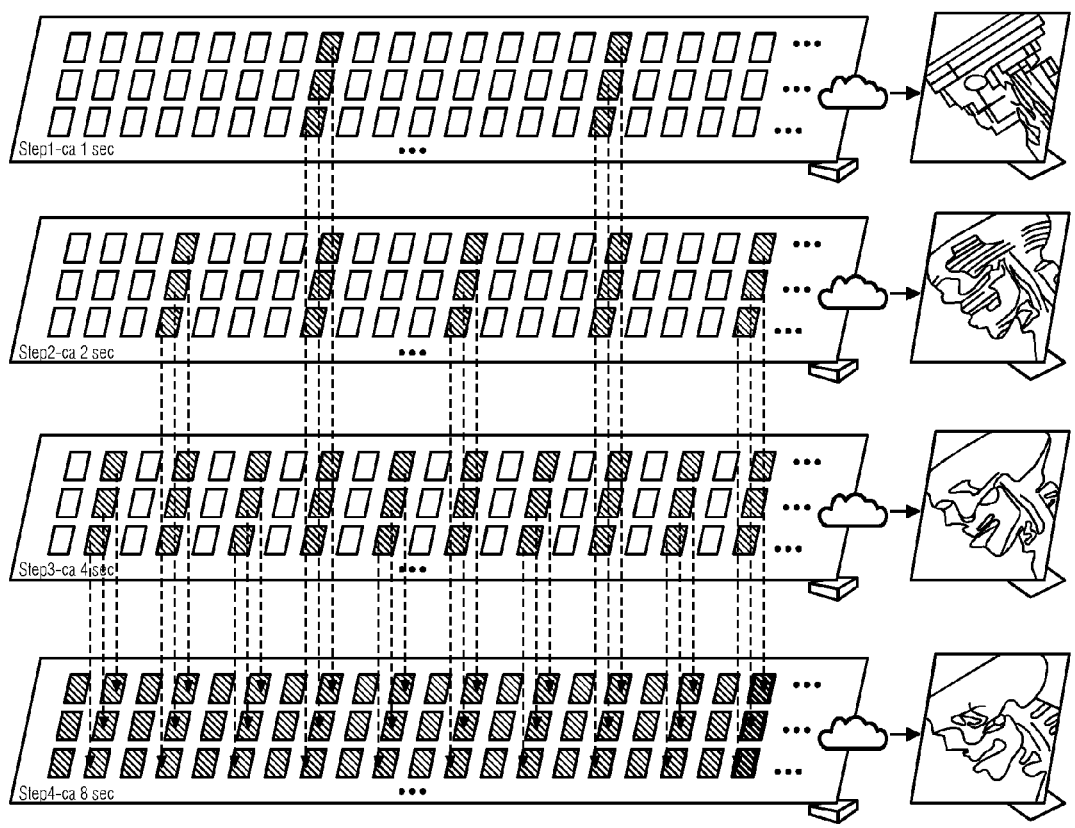
FIG. 2 shows an example of an embodiment of the inventive loading steps.
Figure 4:
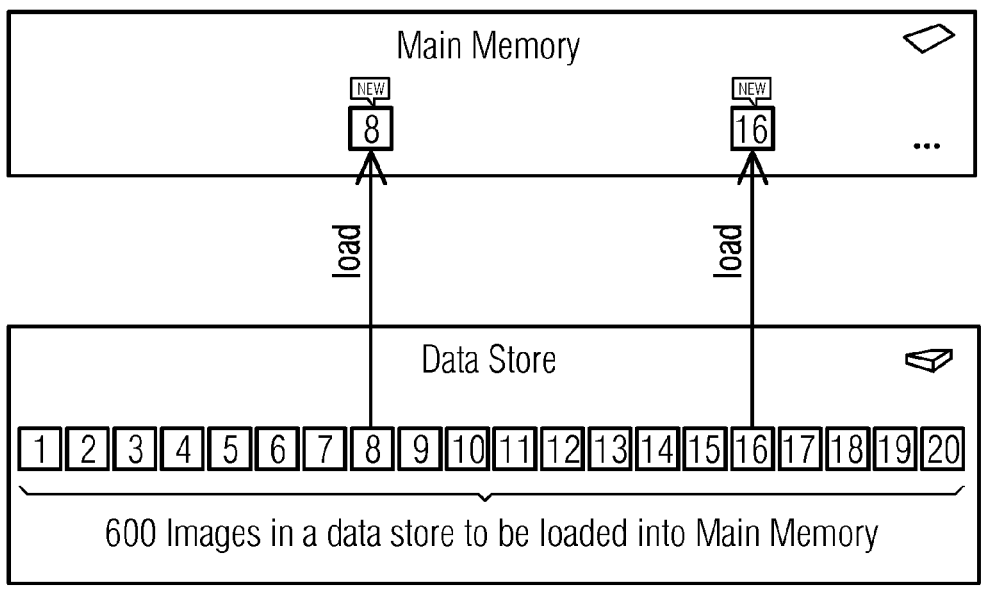
FIG. 4 and FIG. 5 show schematic diagrams at least of the first steps of an embodiment of the inventive loading process.
Figure 5:
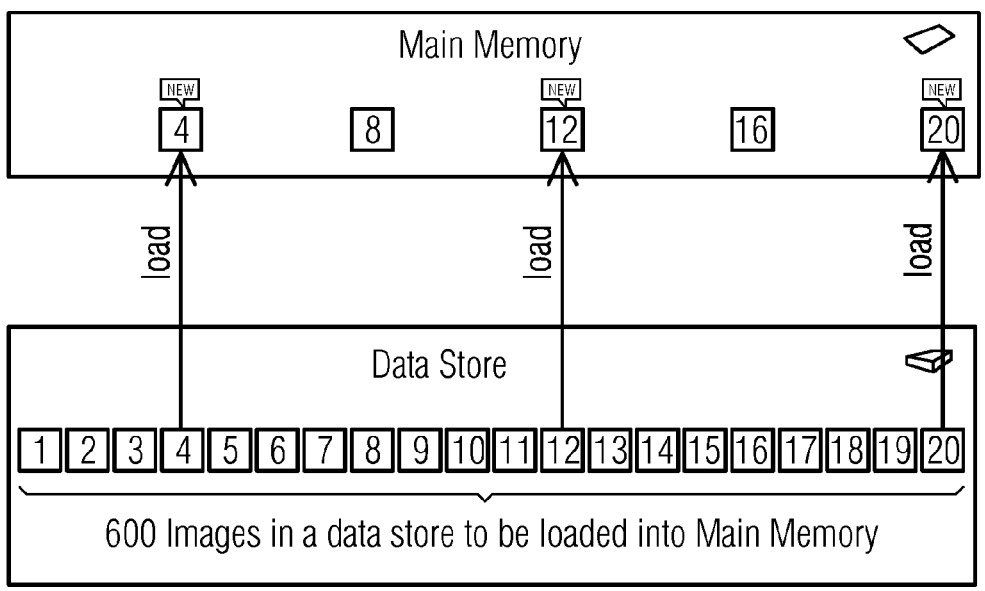
Figure 6:
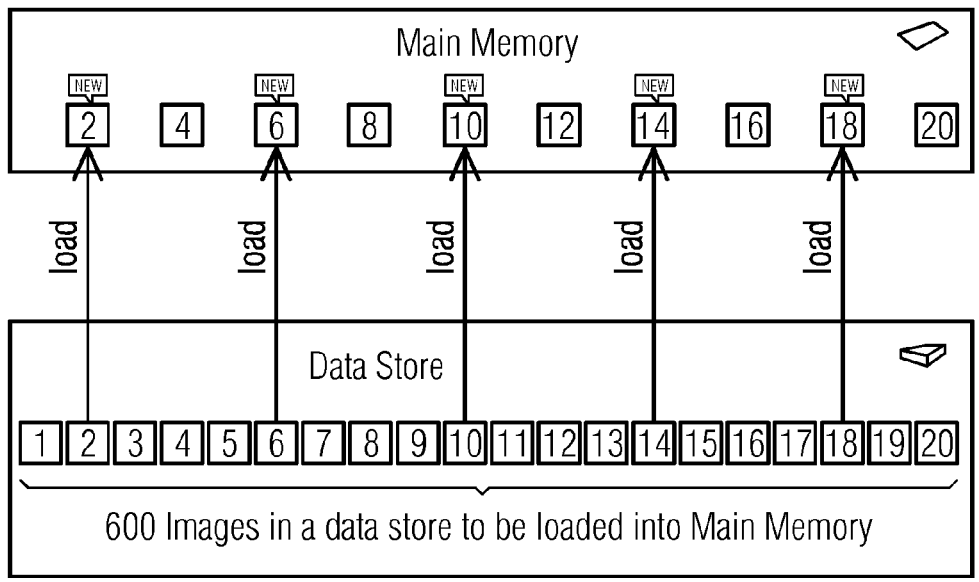
FIG. 6 and FIG. 7 show schematic diagrams at least of further steps of an embodiment of the inventive loading process.
Figure 7:
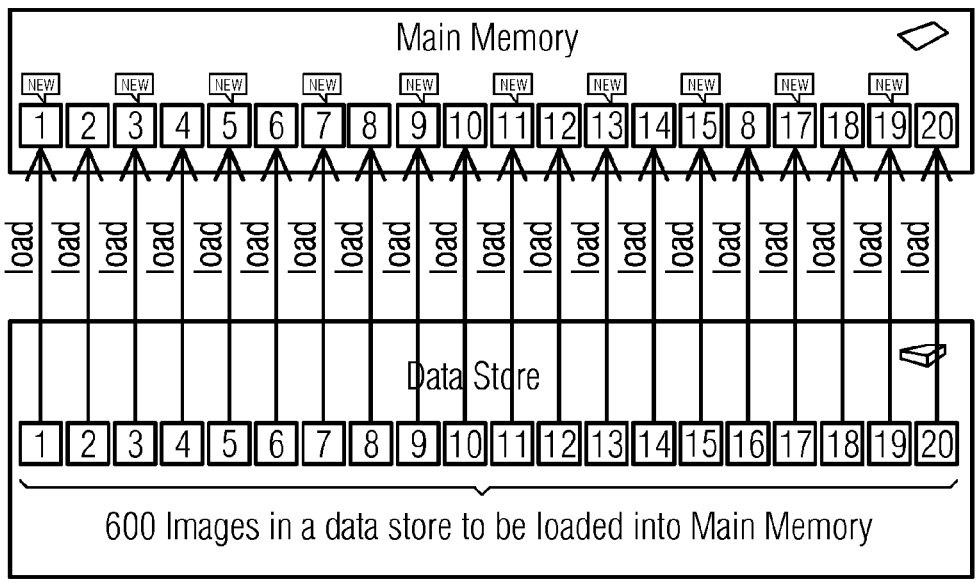
Figure 8:
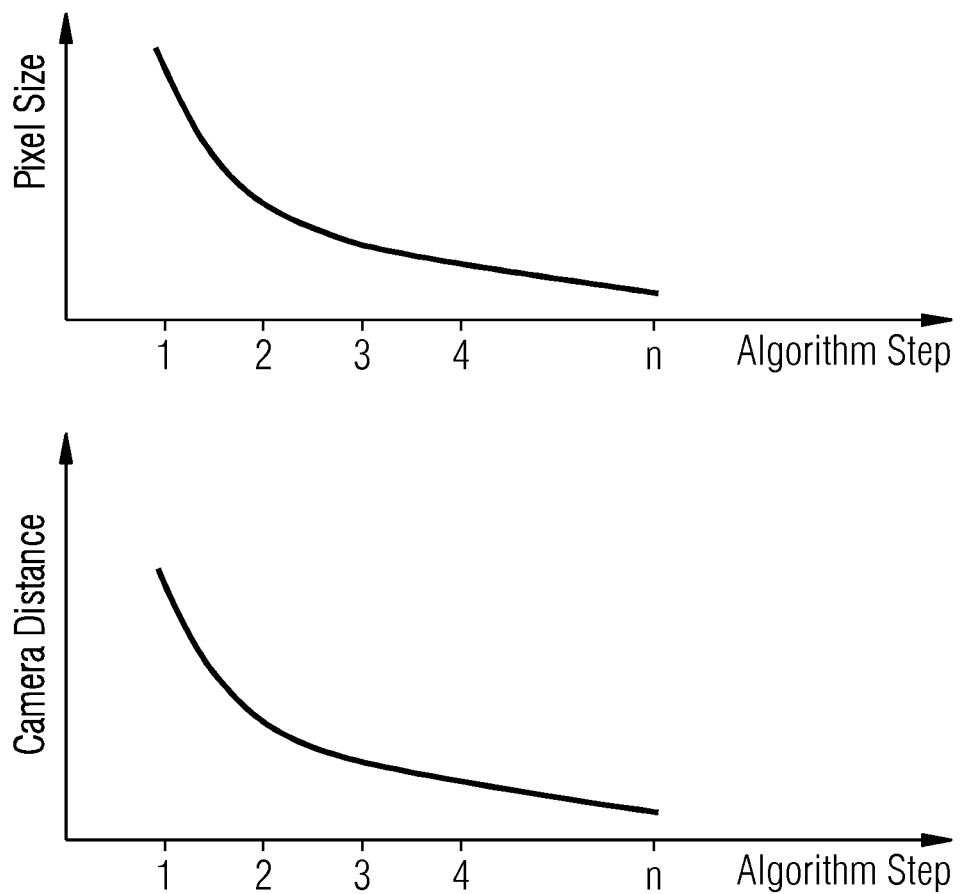
FIG. 8 shows a diagram of the curve for certain pixel sizes and a diagram of the curve for a certain camera distance.
Figure 9:
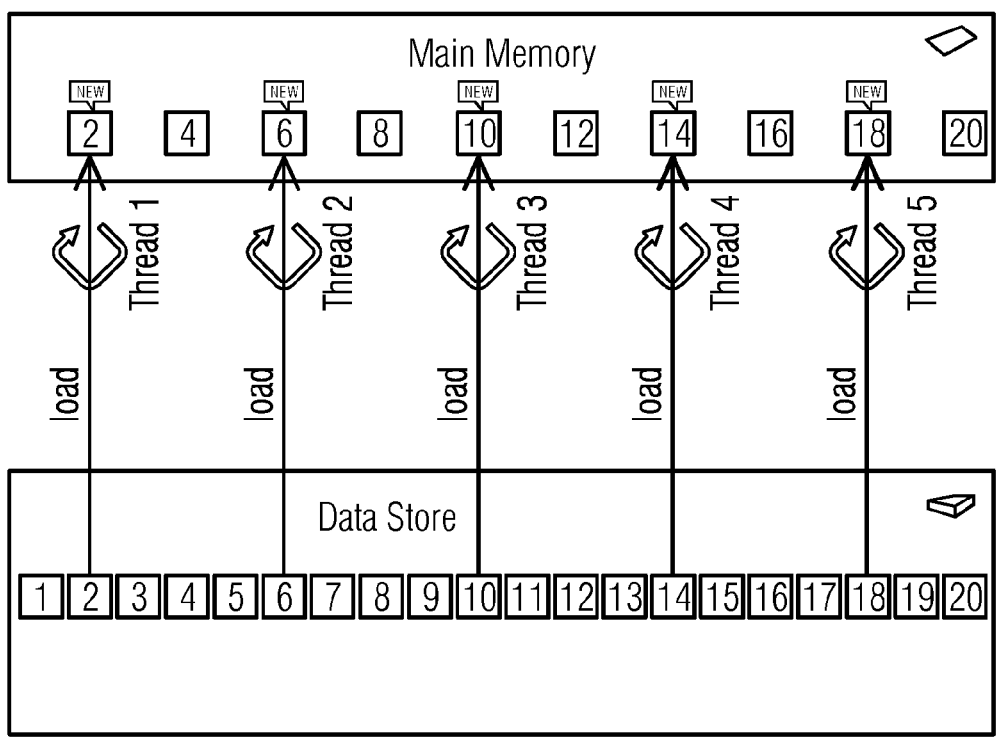
FIG. 9 shows a schematic diagram at least of steps of an embodiment of the inventive loading process for 4-dimensional medical images.
Figure 10:
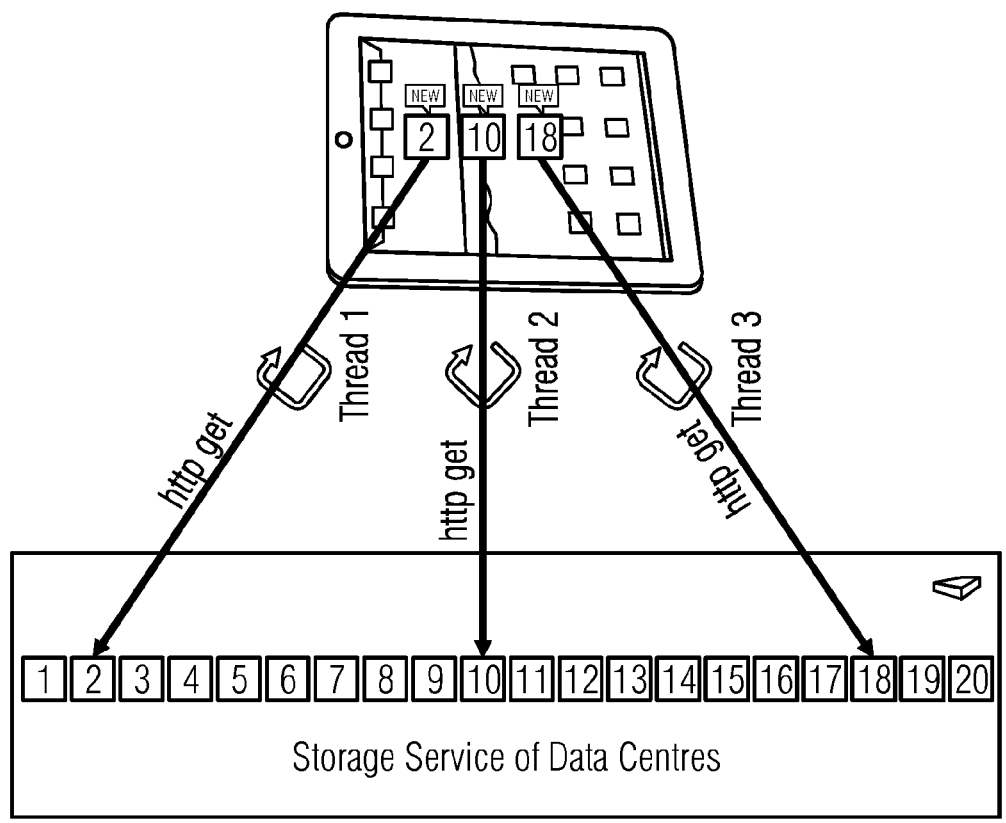
FIG. 10 shows an embodiment of the inventive loading process in conjunction with a tablet PC and a data center.

According to the invention a method is provided for the progressive loading of images of a 3D volume from a data store or database into the main memory of a client and subsequent, progressive 3D volume rendering. The method has the following sequence steps or properties, as shown for example in FIGS. 1 and 2 and at least partially in FIGS. 11 and 14:

Steps:
1 The user always sees the first rendered 3D image without waiting times for any volume size. For this the first n (n≤78 is favorable as this number of images can be loaded in all standard medical instances in less than one second) images $M_1$ to $M_{n-1}$ are first loaded from a data store into the main memory, being distributed in a regular manner over the volume. These images are transferred to the volume renderer for volume rendering. Both the voxel size and camera distance are determined based on the number of images loaded.

2 In the second step approximately the same number of images, also distributed evenly over the volume, are loaded into the main memory taking into account the images already loaded in the first step, so that an image is not loaded more than once and the images loaded in total in the two steps are distributed in a regular manner over the volume. The waiting time in the second step is approximately equal to that in the first and is not perceived by the user. Both the voxel size and the camera distance are determined based on the number of images loaded in both steps. These parameters are used to perform a volume rendering process.

3 In the third step, if necessary, twice as many images are loaded as in the second step (exponential increase by the factor $2^x$). The distribution of all loaded images (in the preceding steps and in the current step) remains regular in the volume. Both the voxel size and the camera distance are determined based on the number of images loaded in the preceding steps and in the current step. These parameters are used to perform a volume rendering process.

4 Step 3 is repeated either until it is terminated by the user or until all the images of the volume have been loaded into the main memory.

In one embodiment of the invention the method described above can be applied to 4D images or data, as set out below.

The method for displaying medical 4D data on any devices with access to data in any data centers operates by way of example as follows:

Every volume in the 4D study to be displayed is divided into sets of images (image sets), it being more favorable for the following criteria to be satisfied:

The sets of images of each volume have no overlaps, in other words they are distinct. An image can be found in just one image set S.

An image set S contains images which are distributed evenly over the volume.

The number of images in the first image set $S_1$ is determined in such a manner that the images can all be loaded and rendered in one second for a specified device, a specified data location and a specified network.

The number of images in each further image set $S_N$ is twice as large as in the image set $S_{N-1}$.

Figure 11:
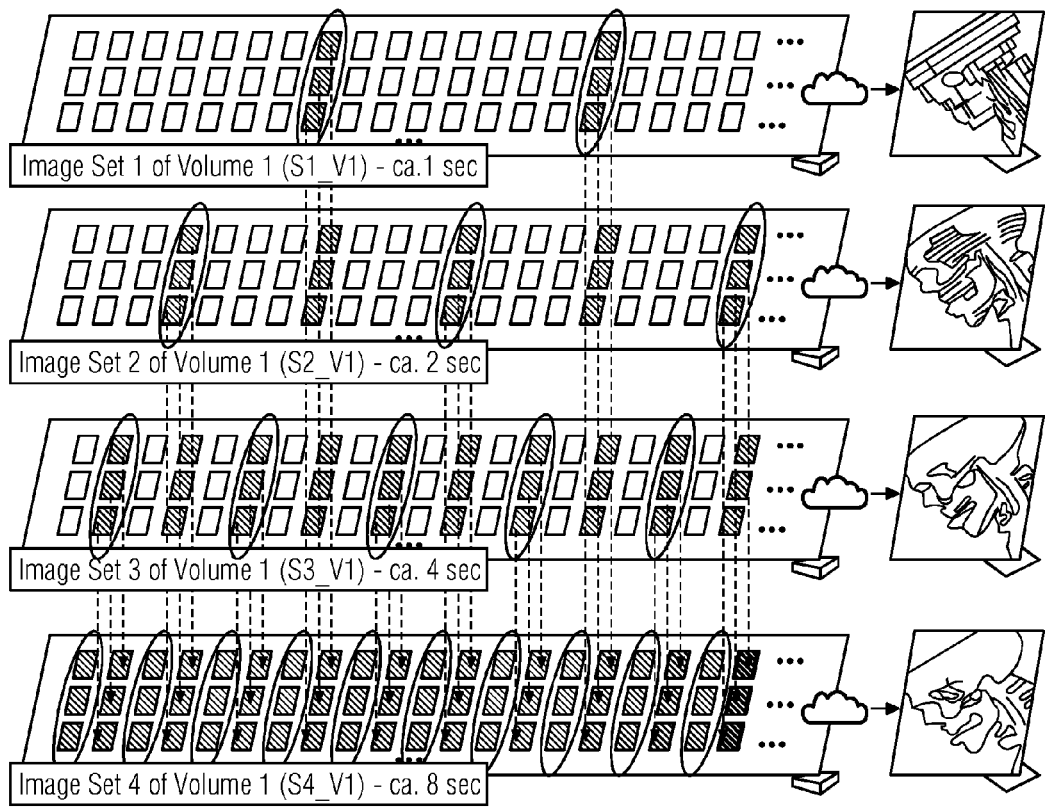
FIG. 11 shows an embodiment of the inventive loading process in the context of 4D images.

The formation of the data sets with corresponding properties for a 3D volume of the 4D study is shown by way of example in FIG. 11.

The image sets of different volumes of a 4D study—as shown in FIG. 12—are loaded. The loading sequence in particular is of particular importance.

The loading sequence of the individual subsets of 3D volumes of a 4D data set is determined—as illustrated in FIG. 13.

In FIG. 13 it is illustrated that the first set of each individual volume is loaded first: S1_V1, S1_V2, S1_V3. The number of images in these data sets is selected so that they can each be rendered in one second.

The image sets S2_V1, S2_V2, S2_V3 and so on follow. It is important that the method also operates for different sizes of individual 3D volumes.

The data sets are simply loaded using a virtual "round robin" method until all the sets have been loaded.

The volumes of a step, such as for example for step 1: S1_V1, S1_V2 and S1_V3, can be loaded in a parallel manner. The volumes of subsequent steps are therefore not loaded in a parallel manner, as the user can intervene to terminate before the steps are reached.

The complete loading algorithm is shown for example in FIG. 14.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the progressive loading of medical, multidimensional images into a medical application, the method comprising steps of:
    a) loading a first number n of image sets with an image set size $k^y$, the $k^y$ images of which are distributed in a regular manner over a volume, which is to be loaded in its entirety as a result;
    b) loading a number $n^x$ of image sets starting with a factor x=1, with the images loaded in total in the preceding and current steps being distributed in a regular manner over the volume;
    c) determining a camera distance and voxel size based on the number of images loaded in the preceding and current steps, the camera distance and voxel size being suitable as parameters for a volume rendering; and
    d) repeating the steps b) and c) while increasing the number of image sets with a factor x=x+1, at least one of
        until all the images of the volume have been loaded in their entirety, and
        until termination of the method, wherein n=2.

2. The method of claim 1, further comprising:
    repeating of steps b) and c) of claim 1 while increasing the image set size with a factor y=y+1, at least one of
        until all the images of the volume have been loaded in their entirety, and
        until the termination of the method.

3. The method of claim 2, wherein k=2.

4. The method of claim 1, wherein y=0.

5. The method of claim 1, wherein y=1.

6. The method of claim 1, wherein k=2.

7. The method of claim 1, wherein the image sets are distinct.

8. The method of claim 1, wherein an image is only loaded once.

9. The method of claim 1, wherein $k^y$ is determined so that the rendering of the volume is performable within a time interval of 1 second.

10. An apparatus for the progressive loading of medical, multidimensional images into a medical application, comprising:
a processor configured to:
a) load a first number n of image sets with an image set size $k^y$, the $k^y$ images of which are distributed in a regular manner over a volume, which is to be loaded in its entirety as a result;
b) load a number $n^x$ of image sets starting with a factor x=1, with the images loaded in total before and currently being distributed in a regular manner over the volume;
c) determine a camera distance and voxel size based on the number of loaded images, the camera distance and voxel size being suitable as parameters for a volume rendering; and
d) repeat the loading of the number $n^x$ of image sets and the determining while increasing the number of image sets with a factor x=x+1, at least one of until all the images of the volume have been loaded in their entirety and until termination of the loading and determining, wherein n=2.

11. The apparatus of claim 10, wherein the processor is configured to repeat the loading and the determining while increasing the image set size with a factor y=y+1, at least one of until all the images of the volume have been loaded in their entirety and until termination of the loading and determining.

12. The apparatus of claim 11, wherein y=0.

13. The apparatus of claim 11, wherein y=1.

14. The apparatus of claim 10, wherein the apparatus is a server.

15. A non-transitory computer readable medium including program segments for, when executed on a computer device, causing the computer device to implement the method of claim 1.

* * * * *